(12) United States Patent
Lindsay et al.

(10) Patent No.: US 8,197,405 B2
(45) Date of Patent: Jun. 12, 2012

(54) SURGICAL RETRACTOR ASSEMBLY AND ASSOCIATED METHOD OF USE

(75) Inventors: G. Mark Lindsay, Fort Wayne, IN (US); Priya R. Prasad, Miami, FL (US); Stephen R. Donnelly, Willoughby, OH (US)

(73) Assignee: DePuy Products, Inc., Warsaw, IN (US)

( * ) Notice: Subject to any disclaimer, the term of this patent is extended or adjusted under 35 U.S.C. 154(b) by 715 days.

(21) Appl. No.: 12/326,935

(22) Filed: Dec. 3, 2008

(65) Prior Publication Data

US 2010/0137692 A1 Jun. 3, 2010

(51) Int. Cl.
*A61B 1/32* (2006.01)
(52) U.S. Cl. .................. 600/235; 606/86 B; 606/280
(58) Field of Classification Search ................ D24/135; 600/201–246; 606/96, 99, 86 B
See application file for complete search history.

(56) References Cited

U.S. PATENT DOCUMENTS

| 278,520 | A | * | 5/1883 | Doyle | 600/242 |
|---|---|---|---|---|---|
| 2,695,607 | A | * | 11/1954 | Hipps et al. | 600/210 |
| 3,651,800 | A | * | 3/1972 | Wilbanks | 600/210 |
| 3,890,960 | A | * | 6/1975 | Wunsch et al. | 600/191 |
| 3,916,910 | A |  | 11/1975 | Seeling et al. |  |
| 4,155,355 | A | * | 5/1979 | Yamamoto | 600/233 |
| 4,232,660 | A | * | 11/1980 | Coles | 600/210 |
| 4,610,243 | A |  | 9/1986 | Ray |  |
| 4,686,972 | A | * | 8/1987 | Kurland | 606/96 |
| 5,217,463 | A |  | 6/1993 | Mikhail |  |
| D358,470 | S | * | 5/1995 | Quigley et al. | D24/135 |
| 5,743,853 | A |  | 4/1998 | Lauderdale |  |
| 5,971,920 | A |  | 10/1999 | Nagel |  |
| D422,705 | S | * | 4/2000 | Koros et al. | D24/135 |
| D457,956 | S | * | 5/2002 | Koros et al. | D24/135 |
| 7,909,829 | B2 | * | 3/2011 | Patel et al. | 606/86 A |
| 2002/0198533 | A1 | * | 12/2002 | Geisler et al. | 606/96 |
| 2004/0267274 | A1 | * | 12/2004 | Patel et al. | 606/96 |
| 2005/0080418 | A1 | * | 4/2005 | Simonson et al. | 606/61 |
| 2007/0043265 | A1 |  | 2/2007 | Rochetin |  |
| 2007/0244489 | A1 | * | 10/2007 | Patel et al. | 606/96 |

OTHER PUBLICATIONS

Stanley Hoppenfeld and Piet DeBoer, Figures 2-6 and 2-7, "Surgical Exposures in Orthopaedics, The Anatomic Approach", 2003, p. 73, Third Edition, published by Lippincott, Williams & Wilkins (1 page).
Kmedic, "Orthopedic Sourcebook, Instruments for Surgeons", 2008, p. B/19, published by Teleflex Medical, Inc. (1 page), available at: http://www.teleflexmedical.com/prod_kmedic_branded.php.
Page B19 of Kmedic "Orthopaedic Sourcebook" published by Teleflex Medical, Inc. at: http://www.teleflexmedical.com/prod_kmedic_branded.php; Published at least as early as Dec. 2, 2008.

* cited by examiner

*Primary Examiner* — Eduardo C Robert
*Assistant Examiner* — Mary Hoffman
(74) *Attorney, Agent, or Firm* — Maginot, Moore & Beck

(57) ABSTRACT

A surgical retractor assembly is disclosed that includes a bone plate and a retractor. The bone plate has a tapered end portion. The retractor includes a base having (i) a body defining a bottom surface and a distal portion, the distal portion defining a distal surface, (iii) a first pair of tabs extending from the body that are spaced apart from each other, and (iv) a second pair of tabs extending from the body that are spaced apart from each other. The retractor further includes a handle attached to the base. The first pair of tabs and the bottom surface define a first plate space. The second pair of tabs and the distal surface define a second plate space.

10 Claims, 6 Drawing Sheets

SURGICAL RETRACTOR ASSEMBLY AND ASSOCIATED METHOD OF USE

BACKGROUND

The present disclosure relates generally to a surgical retractor assembly and an associated method of using of the retractor assembly.

In a surgical procedure in which a bone plate is attached to a fractured long bone, a surgeon creates an incision in a patient to expose a portion of the fractured long bone. Thereafter, the bone plate is advanced through the incision to a location adjacent to the long bone. Then, a drill is advanced in alignment with one of the central screw openings in the bone plate and a hole is drilled in the bone in alignment with the central screw opening. A screw is thereafter advanced through the incision and screwed into the bone through the central screw opening.

After the bone plate is partially attached to the fractured long bone with the bone screw as described above, it may be necessary to pull a patient's tissue to expose the other screw openings in the bone plate such as the terminal screw openings. Common Hohman surgical retractors have been used achieve the above exposure. For example, a Hohman surgical retractor has a finger at a distal end of the retractor. The retractor is then oriented transverse to the axis of the long bone, and the finger of the retractor is urged against the fractured bone and/or side edge of the bone plate. Then, the retractor is pivoted to act as a second class lever to pull the patient's tissue in a direction transverse to the axis of the long bone so as to expose a portion of the bone plate. By using a number of Hohman retractors simultaneously, the surgeon can typically expose enough of the bone plate and fractured bone to access all the bone screw holes of the bone plate including the terminal ones at its most extreme proximal end portion and distal end portion to carry out the above-described bone drilling and bone screw placement.

When performing a minimally invasive surgical procedure to attach a bone plate to a fractured long bone, a surgeon may create an incision that is significantly shorter than the bone plate which is being implanted. Working through the relatively small incision, a drill may be advanced in alignment with one of the central screw openings in the bone plate and a hole is drilled in the bone in alignment with the central screw opening. A screw is thereafter advanced through the small incision and screwed into the bone through the central screw opening in typical fashion. However, retraction of the patient's tissue in a direction transverse to the axis of the long bone with Hohman retractors often times is not adequate to expose the terminal bone screw holes located in the distal and proximal end portions of the bone plate.

What is needed therefore is an improved retractor that is able to be used with a bone plate to adequately expose all the bone screw openings of the bone plate including the terminal openings. What is further needed is an improved retractor that is able to be used with a bone plate to adequately expose all the bone screw openings of the bone plate when the bone plate is implanted through a relatively small incision.

SUMMARY

In accordance with one embodiment of the present disclosure, there is provided a surgical retractor assembly that includes a bone plate and a retractor. The bone plate has a tapered end portion. The retractor includes a base having (i) a body defining a bottom surface and a distal portion, the distal portion defining a distal surface, (iii) a first pair of tabs extending from the body that are spaced apart from each other, and (iv) a second pair of tabs extending from the body that are spaced apart from each other. The retractor further includes a handle attached to the base. The first pair of tabs and the bottom surface define a first plate space. The second pair of tabs and the distal surface define a second plate space. The retractor is positionable in relation to the bone plate between a first position and a second position. When the retractor is positioned in the first position, (i) the bone plate is positioned in the first plate space, and (ii) the bone plate is located outside of the second plate space. When the retractor is positioned in the second position, (i) the bone plate is positioned in the second plate space, and (ii) the bone plate is located outside of the first plate space.

Pursuant to another embodiment of the present disclosure, there is provided a surgical retractor that includes a base having (i) a body defining a bottom surface and a distal portion, the distal portion defining a distal surface, (iii) a first pair of tabs extending from the body that are spaced apart from each other, and (iv) a second pair of tabs extending from the body that are spaced apart from each other. The surgical retractor further includes a handle attached to the base. The first pair of tabs and the bottom surface define a first plate space configured to receive a first portion of a bone plate therein. The second pair of tabs and the distal surface define a second plate space configured to receive a second portion of the bone plate therein.

In accordance with yet another embodiment of the present disclosure, there is provided a method of retracting tissue near a bone plate exposed through an incision defined in a body. The method includes providing a retractor that has a base which includes (i) a bottom surface, (ii) a distal surface, (iii) a first pair of tabs that are spaced apart from each other, and (iv) a second pair of tabs that are spaced apart from each other, the first pair of tabs and the bottom surface defining a first plate space, the second pair of tabs and the distal surface defining a second plate space. The method further includes positioning the retractor in relation to the bone plate in a first position in which (i) the bone plate is located in the first plate space, and (ii) the bone plate is located outside of the second plate space. Also, the method includes advancing the retractor in relation to the bone plate along an axis of the bone plate after the positioning step from the first position to an intermediate position while the bone plate is located in the first plate space. The method additionally includes moving the retractor in relation to the bone plate from the intermediate position to a second position in which (i) the bone plate is positioned in the second plate space, and (ii) the bone plate is located outside of the first plate space. The method also includes retracting tissue in relation to an end portion of the bone plate in response to the moving step.

DESCRIPTION OF THE PREFERRED EMBODIMENTS

Figure 1:
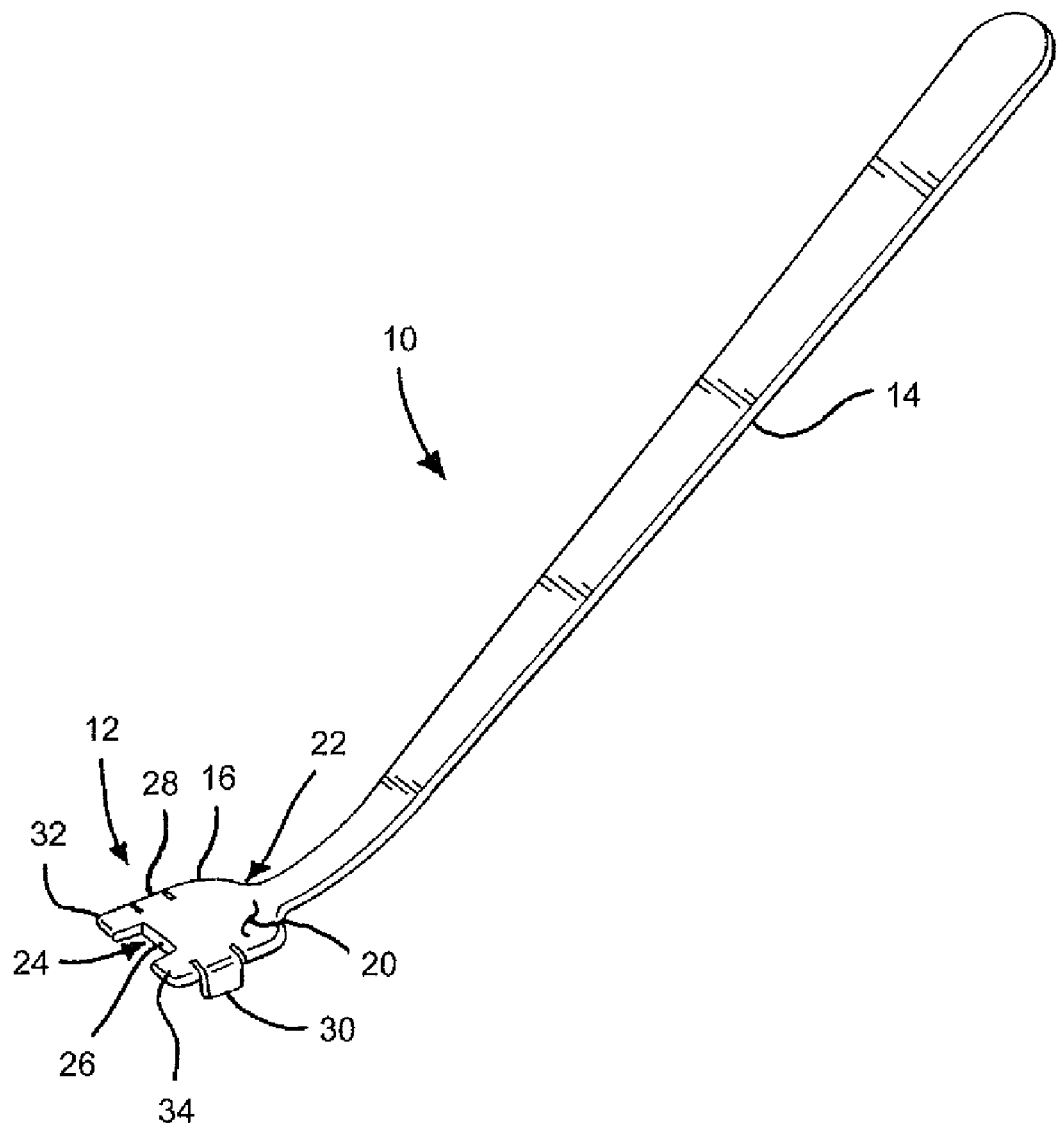
FIG. 1 is a perspective view of the retractor of the assembly of the present disclosure.

While the retractor, associated assembly, and associated method described herein is susceptible to various modifications and alternative forms, specific embodiments thereof have been shown by way of example in the drawings and will herein be described in detail. It should be understood, however, that there is no intent to limit the retractor, associated assembly, and associated method to the particular forms disclosed, but on the contrary, the intention is to cover all modifications, equivalents, and alternatives falling within the spirit and scope of the invention as defined by the appended claims.

Figure 2:
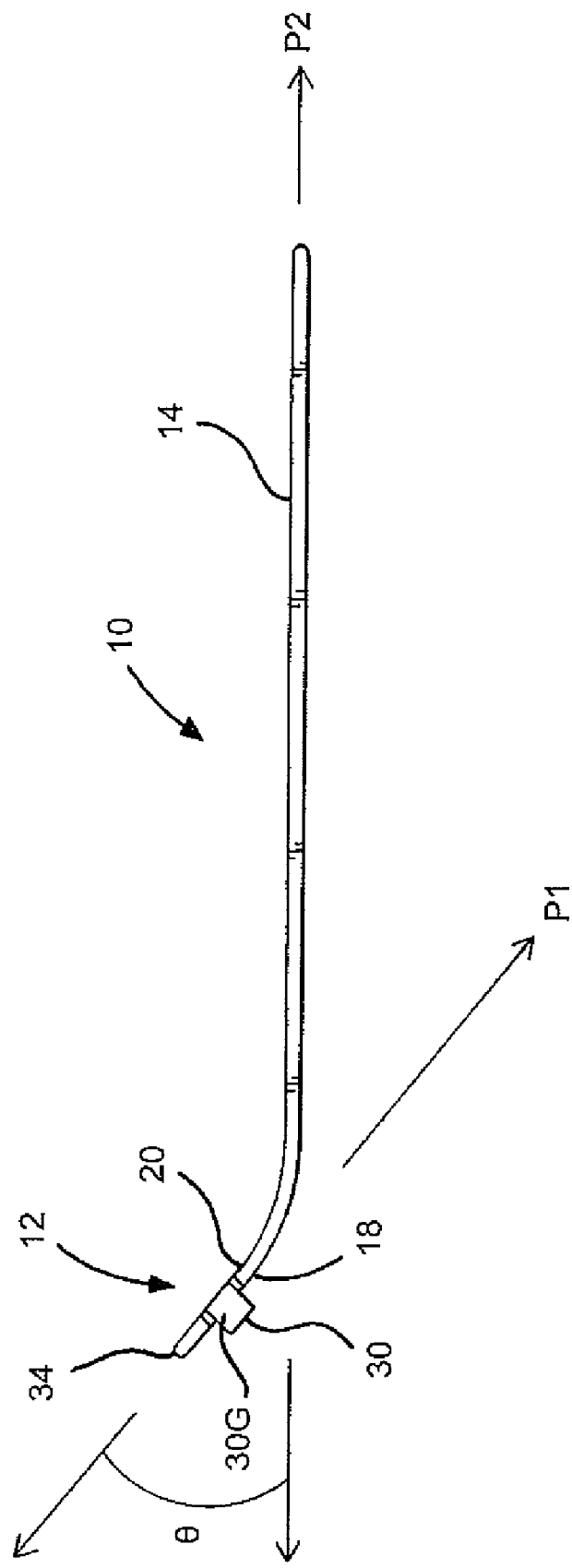
FIG. 2 is a side elevational view of the retractor of FIG. 1.

Referring now to FIGS. 1-6, there is shown a retractor 10 configured in accordance with the present disclosure. The retractor 10 includes a base 12 and a handle 14 that are attached together. The base 12 includes a body 16 that defines a bottom surface 18 and a top surface 20. The bottom surface 18 defines a first plane P1 as shown in FIG. 2. The handle 14 defines a second plane P2 that is aligned with the axis of the handle. The first plane P1 and the second plane P2 intersect to define an angle Θ. Preferably, the angle Θ is between 120° and 160°. More preferably, the angle Θ is between 130° and 150°. And most preferably, the angle Θ equals 141°. The base 12 further includes a proximal portion 22 and a distal portion 24. The handle 14 is attached to the proximal portion 22. The distal portion 24 defines a distal surface 26.

Figure 3:
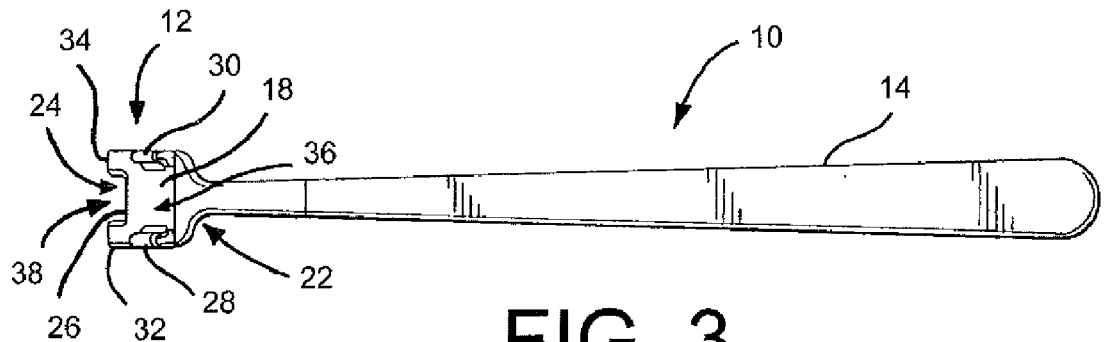
FIG. 3 is a bottom elevational view of the retractor of FIG. 1.
Figure 4:
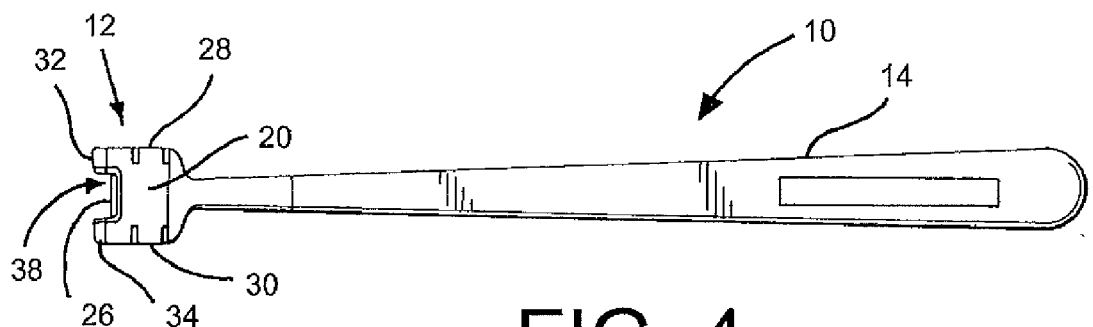
FIG. 4 is a top elevational view of the retractor of FIG. 1.
Figure 5:
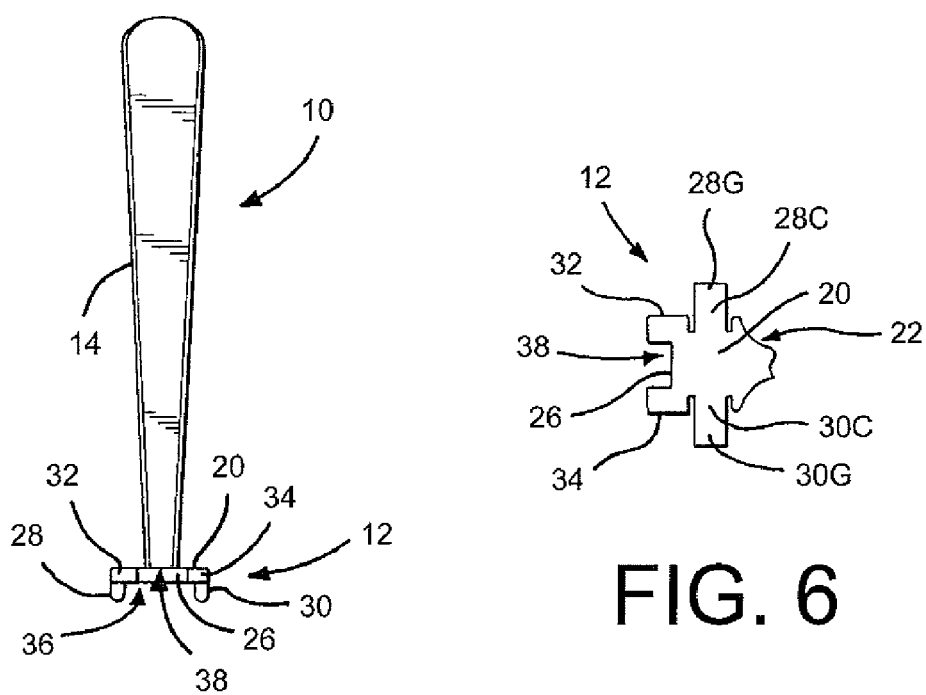
FIG. 5 is a front elevational view of the retractor of FIG. 1.
Figure 6:
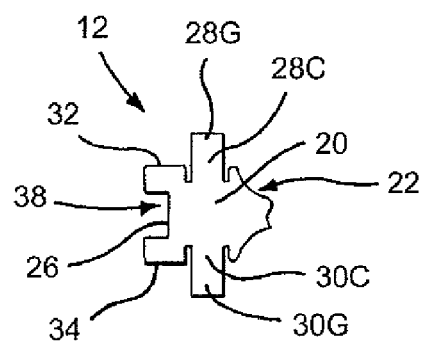
FIG. 6 is a fragmentary top elevational view of the retractor of FIG. 1 prior to a manufacturing step of bending the tabs so as form a pair of L-shaped tabs.

The base 12 further includes a pair of tabs 28, 30. The tab 28 is spaced apart from the tab 30. Each tab 28, 30 includes a portion that extends downwardly in relation to the bottom surface 18 of the body 16 as shown in FIGS. 2, 3, and 5. More specifically, the tab 28 is configured as an L-shaped member that includes a connecting portion 28C and a guide portion 28G. The connecting portion 28C extends laterally outwardly from a lateral side surface of the body 16. The guide portion 28G is attached to the connecting portion 28C and extends perpendicularly thereto in a downward direction in relation to the bottom surface 18. Similarly, the tab 30 is configured as another L-shaped member that includes a connecting portion 30C and a guide portion 30G. The connecting portion 30C extends laterally outwardly from another lateral side surface of the body 16. The guide portion 30G is attached to the connecting portion 30C and extends perpendicularly thereto in a downward direction in relation to the bottom surface 18. The pair of tabs 28, 30 and the bottom surface 18 define a first plate space 36 as shown in FIGS. 3 and 5.

The base 12 further includes another pair of tabs 32, 34 that extend distally from the body 16 as shown in FIGS. 1-6. The tab 32 is spaced apart from the tab 34. The pair of tabs 32, 34 and the distal surface 26 define a plate space 38 as shown in FIGS. 3-6.

Figure 7:
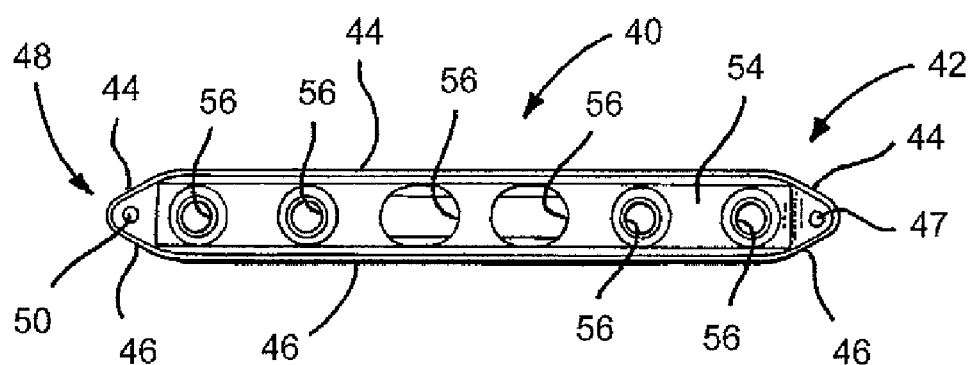
FIG. 7 is a top elevational view of the bone plate of the assembly of the present disclosure.
Figure 8:
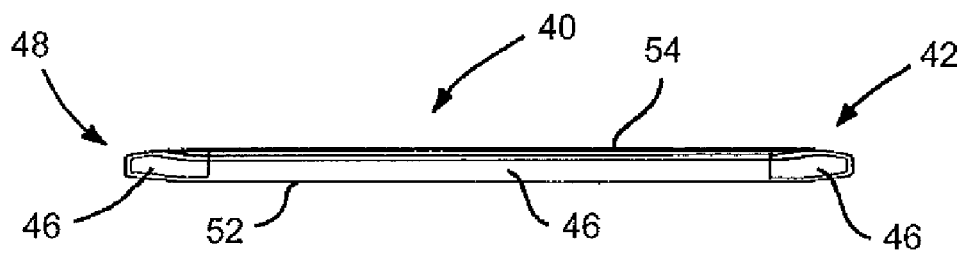
FIG. 8 is a side elevational view of the bone plate of FIG. 7.
Figure 9:
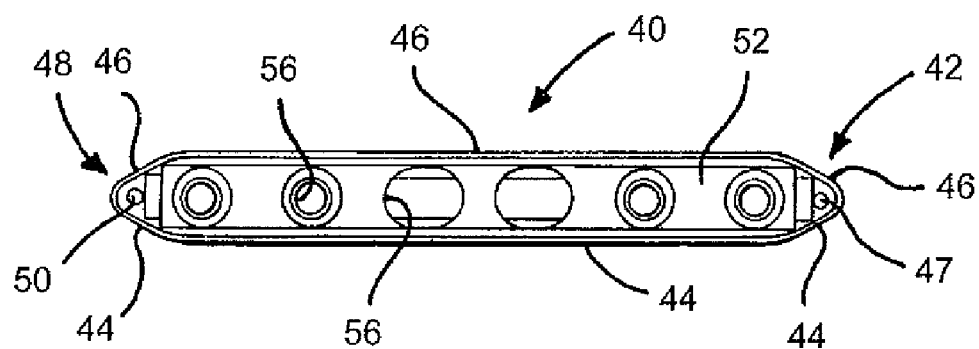
FIG. 9 is a bottom elevational view of the bone plate of FIG. 7.

Referring now to FIGS. 7-9, there is shown a bone plate 40 configured in accordance with the present disclosure. The bone plate 40 of FIGS. 7-9 and the retractor 10 of FIGS. 1-6 cooperate with each other in a beneficial manner to form an assembly 5 as will be discussed further below. The bone plate 40 is configured so that its bone contacting side may be received in juxtaposition to a patient's bone such a fibula, humerus, radius, ulna, tibia, or clavicle.

The bone plate 40 includes a tapered end portion 42 and defines a lateral side wall 44 and another lateral side wall 46. The tapered end portion 42 defines a suture hole 47. The bone plate 40 further includes another tapered end portion 48 that defines another suture hole 50. The bone plate defines a bone contact side 52 and an opposite top side 54. A plurality of screw holes 56 are also defined in the bone plate 40. The screw holes 56 may be all threaded or non-threaded or may be a combination of threaded and non-threaded holes as is common in the art. In any event, the screw holes 56 are configured to receive bone screws therein.

Figure 10:
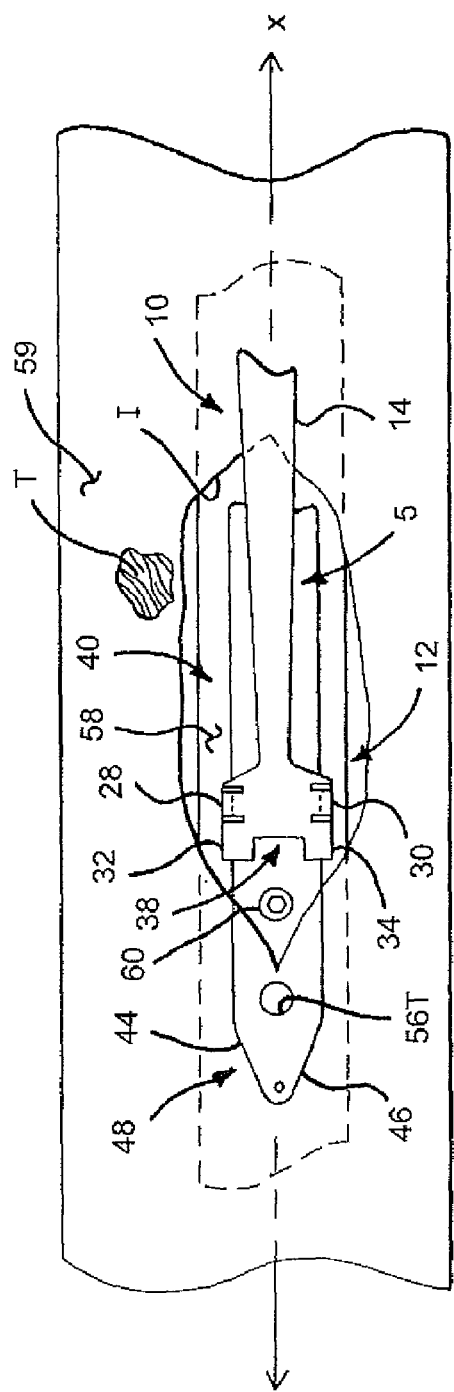
FIG. 10 is a fragmentary, top elevational view of the assembly of the present disclosure including the retractor of FIG. 1 and the bone plate of FIG. 7 located within a patient's body and partially visible through an incision, and with the retractor positioned at its first position in relation to the bone plate.
Figure 11:
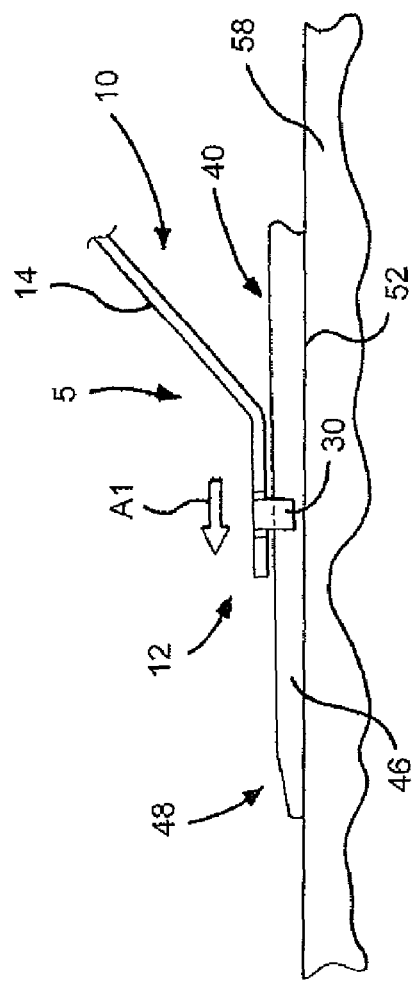
FIG. 11 is a fragmentary side elevational view of the assembly of FIG. 10, with most of the patient's body shown removed for clarity of viewing.

The assembly 5 is shown being used in FIGS. 10-14 in accordance with the present disclosure. In particular, FIG. 10 shows the bone plate 40 partially secured to a radius bone 58 of a patient 59 by a bone screw 60 passing through one of the screw holes 56 defined in the bone plate 40. The bone plate 40 is partially exposed through an incision I defined in the patient. FIGS. 10 and 11 also show the retractor 10 positioned in relation to the bone plate 40 in a first position in which the bone plate 40 is positioned in the first plate space 36. When the retractor 10 is located in the first position as shown in FIGS. 10 and 11, the bone plate 40 is located outside of the second plate space 38. FIG. 11 is a side elevational view of the assembly 5 and associated radius bone 58 of FIG. 10, with the other portions of the patient's body removed for clarity of description.

Figure 13:
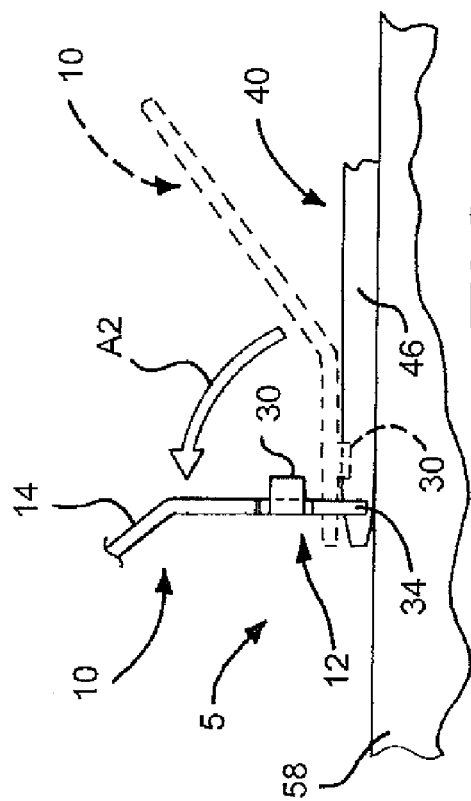
FIG. 13 is a fragmentary side elevational view of the assembly of FIG. 12, with most of the patient's body shown removed for clarity of viewing.

After the retractor 10 is positioned as shown in FIGS. 10 and 11, the retractor 10 is advanced in sliding contact with the bone plate 40 in the direction of arrow A1 along an axis X of the bone plate 40 to an intermediate position shown in phantom in FIG. 13. It should be appreciated that during movement of retractor 10 from its first position shown in FIG. 10 to its intermediate position shown in phantom in FIG. 13, the bone plate 40 is interposed between the tabs 28 and 30. When the retractor 10 is positioned in the intermediate position, the second plate space 38 is positioned over the tapered end portion 48 of the bone plate 40.

Figure 12:
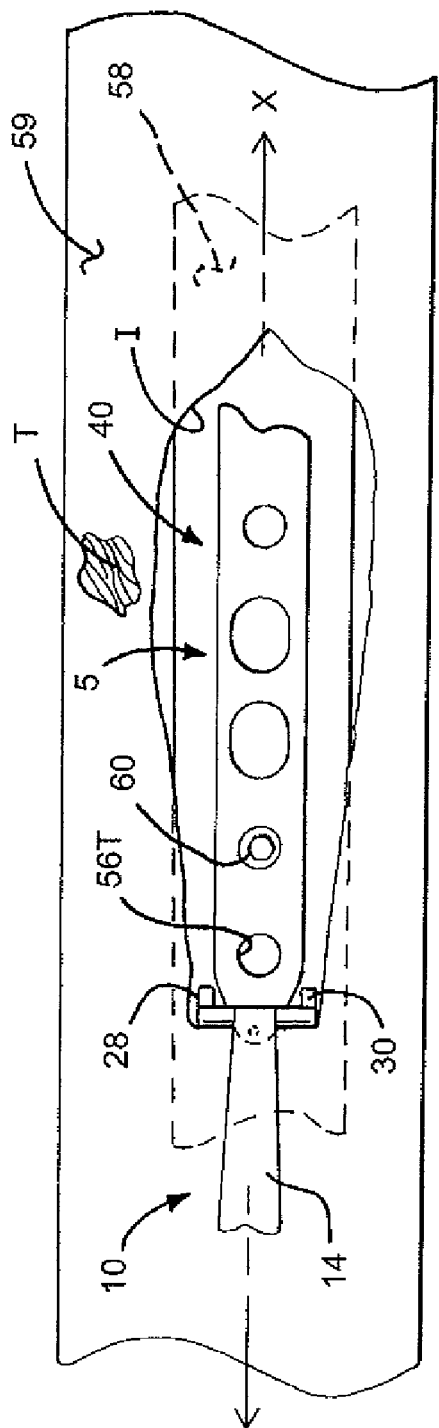
FIG. 12 is a view similar to FIG. 10, but showing the retractor positioned in at its second position in relation to the bone plate.

Thereafter, the retractor 10 is pivoted in relation to the bone plate 40 to a second position as shown in solid in FIG. 13. In particular, the retractor 10 is pivoted in the direction of arrow A2 to the second position as shown in FIG. 13. During such pivoting, the retractor 10 and the bone plate 40 are continuously in contact with one another. Note that during a latter part of such pivoting, the tabs 32, 34 are respectively in contact with both of the lateral side walls 44, 46. Also note that when the bone plate 40 is positioned at the second position as shown in solid in FIG. 13, the retractor 10 is positioned in contact with both of the lateral side walls 44, 46. FIG. 13 is a side elevational view of the assembly 5 and associated radius bone 58 of FIG. 12, with the other portions of the patient's body removed for clarity of description. Note that FIGS. 12 and 13 shows the retractor 10 positioned in relation to the bone screw 40 in the second position in which the bone plate 40 is positioned in the second plate space 38. When the retractor 10 is located in the second position, the tapered end portion 48 of the bone plate 40 is interposed between the tabs 32 and 34. In addition, when the retractor 10 is located in the second position as shown in FIGS. 10 and 11, the bone plate 40 is located outside of the first plate space 36.

Figure 14:
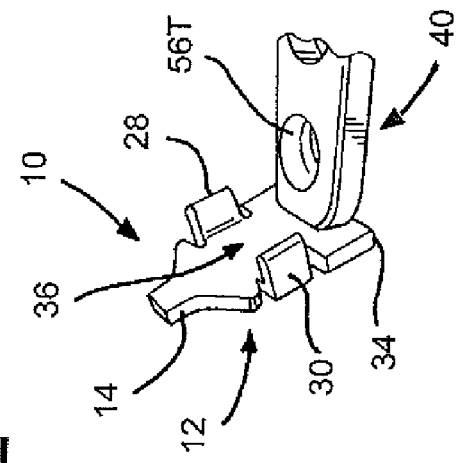
FIG. 14 is a view similar to FIG. 13, but showing the retractor pivoted slightly further in relation to the bone plate than that shown in FIG. 13.

In response pivoting the retractor 10 in relation to the bone plate 40 as discussed above, tissue T of the patient's body 59 is retracted in relation to the tapered end portion 48 of the bone plate 40 thereby exposing a terminal screw hole 56T of the bone plate 40. The retractor 10 is in effect utilized as a lever to retract the patient's tissue T in relation to the bone plate 40. Notice that prior to interaction between the patient's tissue T and the retractor 10, the terminal screw hole 56T is covered up by the patient's tissue T as shown in FIG. 10. FIG. 14 shows the retractor 10 pivoted slightly further in relation to the bone plate 40 if necessary to further retract the patient's tissue T in relation to the bone plate 40.

There is a plurality of advantages arising from the various features of each of the embodiments of the retractor, associated assembly, and associated method described herein. It will be noted that alternative embodiments of the retractor, associated assembly, and associated method may not include all of the features described yet still benefit from at least some of the advantages of such features. Those of ordinary skill in the art may readily devise their own implementations of the retractor, associated assembly, and associated method that incorporates one or more of the features and fall within the spirit and scope of the present invention as defined by the appended claims.

What is claimed is:

1. A surgical retractor assembly, comprising:
a bone plate having a tapered end portion; and
a retractor including:
a base having (i) a body defining a bottom surface and a distal portion, said distal portion defining a distal surface, (iii) a first pair of tabs extending from said body that are spaced apart from each other, and (iv) a second pair of tabs extending from said body that are spaced apart from each other, and
a handle attached to said base,
wherein said first pair of tabs and said bottom surface define a first plate space,
wherein said second pair of tabs and said distal surface define a second plate space,
wherein said retractor is positionable in relation to said bone plate between a first position and a second position,
wherein, when said retractor is positioned in said first position, (i) said bone plate is positioned in said first plate space, and (ii) said bone plate is located outside of said second plate space,
wherein, when said retractor is positioned in said second position, (i) said bone plate is positioned in said second plate space, and (ii) said bone plate is located outside of said first plate space,
wherein:
said first pair of tabs includes a first tab and a second tab,
at least a portion of said first tab extends downwardly in relation to said bottom surface of said body of said base of said retractor, and
at least a portion of said second tab extends downwardly in relation to said bottom surface of said body of said base of said retractor, and
wherein:
said first tab includes a first L-shaped member that has (i) a first connecting portion extending from a first lateral side surface of said body of said base of said retractor, and (ii) a first guide portion attached to said first connecting portion, and
said second tab includes a second L-shaped member that has (i) a second connecting portion extending from a second lateral side surface of said body of said base of said retractor, and (ii) a second guide portion attached to said second connecting portion.

2. The assembly of claim 1, wherein:
said base further has a proximal portion, and
said handle is attached to said proximal portion.

3. The assembly of claim 1, wherein:
said bone plate defines a bone contact side and an opposite side, and
said retractor is positioned in contact with said opposite side of said bone plate when said bone plate is positioned in said first plate space.

4. The assembly of claim 3, wherein:
said tapered end portion of said bone plate defines a first side wall portion and a second side wall portion, and
said retractor is positioned in contact with said first side wall portion and said second side wall portion when said bone plate is positioned in said second plate space.

5. The assembly of claim 1, wherein:
said second pair of tabs includes a third tab and a fourth tab, and
each of said third tab and said fourth tab extends distally from said body of said base of said retractor.

6. The assembly of claim 1, wherein:
said bottom surface of said body of said base of said retractor defines a first plane,
said handle defines a second plane,
said first plane and said second plane intersect to define an angle $\Theta$, and $130° < \Theta < 150°$.

7. A surgical retractor, comprising:
a base having (i) a body defining a bottom surface and a distal portion, said distal portion defining a distal surface, (iii) a first pair of tabs extending from said body that are spaced apart from each other, and (iv) a second pair of tabs extending from said body that are spaced apart from each other, and
a handle attached to said base,
wherein said first pair of tabs and said bottom surface define a first plate space configured to receive a first portion of a bone plate therein,
wherein said second pair of tabs and said distal surface define a second plate space configured to receive a second portion of the bone plate therein,
wherein:
said first pair of tabs includes a first tab and a second tab,
at least a first portion of said first tab extends downwardly in relation to said bottom surface of said body of said base, and
at least a second portion of said second tab extends downwardly in relation to said bottom surface of said body of said base, and
wherein:
said first tab includes a first L-shaped member that has (i) a first connecting portion extending from a first lateral side surface of said body of said base, and (ii) a first guide portion attached to said first connecting portion, and
said second tab includes a second L-shaped member that has (i) a second connecting portion extending from a second lateral side surface of said body of said base of said retractor, and (ii) a second guide portion attached to said second connecting portion.

8. The assembly of claim 7, wherein:
said base further has a proximal portion, and
said handle is attached to said proximal portion.

9. The assembly of claim 7, wherein:
said second pair of tabs includes a third tab and a fourth tab, and
each of said third tab and said fourth tab extends distally from said body of said base.

10. The assembly of claim 7, wherein:
said bottom surface of said body of said base defines a first plane,
said handle defines a second plane,
said first plane and said second plane intersect to define an angle $\Theta$, and $130°<\Theta<150°$.

* * * * *

UNITED STATES PATENT AND TRADEMARK OFFICE
CERTIFICATE OF CORRECTION

| | | |
|---|---|---|
| PATENT NO. | : 8,197,405 B2 | Page 1 of 1 |
| APPLICATION NO. | : 12/326935 | |
| DATED | : June 12, 2012 | |
| INVENTOR(S) | : G. Mark Lindsay et al. | |

It is certified that error appears in the above-identified patent and that said Letters Patent is hereby corrected as shown below:

Column 1,
Line 7, replace "of using of" with --of using--

Column 1,
Line 23, after "used" insert --to--

Column 2,
Line 64, after "as" insert --to--

Column 3,
Line 12, after "in" delete "at"

Column 4,
Line 12, after "such" insert --as--

Column 4,
Line 65, replace "shows" with --show--

Signed and Sealed this
Twenty-sixth Day of February, 2013

Teresa Stanek Rea
*Acting Director of the United States Patent and Trademark Office*